United States Patent [19]

Halstrom

[11] Patent Number: 5,722,828
[45] Date of Patent: Mar. 3, 1998

[54] METHOD OF FABRICATING A DENTAL BITE REGISTRATION MOLD USING A GOTHIC ARCH TRACING

[75] Inventor: Leonard Wayne Halstrom, Lions Bay, Canada

[73] Assignee: Silent Knights Ventures Inc., Vancouver, Canada

[21] Appl. No.: 410,285

[22] Filed: Mar. 24, 1995

[30] Foreign Application Priority Data

Oct. 3, 1994 [CA] Canada ................................. 2133549

[51] Int. Cl.⁶ ...................................................... A61C 19/04
[52] U.S. Cl. ................................... 433/69; 433/73; 433/75
[58] Field of Search ................................. 433/69, 68, 73, 433/75

[56] References Cited

U.S. PATENT DOCUMENTS

| 2,286,288 | 6/1942 | Lover | 433/68 |
|---|---|---|---|
| 2,738,583 | 3/1956 | Green | 433/69 |
| 2,792,629 | 5/1957 | Green | 433/69 |
| 2,863,216 | 12/1958 | Lichtman et al. | 433/69 |
| 4,026,024 | 5/1977 | Tradowsky | 433/68 |

*Primary Examiner*—John J. Wilson
*Attorney, Agent, or Firm*—Oyen Wiggs Green Mutala

[57] ABSTRACT

An apparatus and method for producing a gothic arch tracing representative of the natural range of motion of a patient's mandible. The apparatus consists of a kit including a mandibular bite rim having a tracing plate; a maxillary bite rim having a tracing arm; and a stylus releasably connectable to the tracing arm for extending between the tracing arm and the tracing plate externally of the patient's mouth. The stylus has a marker on one end thereof for drawing a gothic arch tracing on a removable paper substrate, such as a post-it note, attachable to the tracing plate. The tracing is used in the fabrication of a dental bite registration mold for the patient. The mold may in turn be used to mount casts of the patient's dentition in a specific relationship as required for prosthetic or therapeutic purposes.

6 Claims, 4 Drawing Sheets

METHOD OF FABRICATING A DENTAL BITE REGISTRATION MOLD USING A GOTHIC ARCH TRACING

FIELD OF THE INVENTION

This application relates to a kit and technique for producing gothic arch tracings representative of the natural range of motion of a patient's mandible. The tracing is used in the fabrication of a dental bite registration mold for the patient. The mold is in turn used to mount casts of the patient's dentition in a specific relationship as required for prosthetic or therapeutic purposes.

BACKGROUND OF THE INVENTION

The range of motion of the human mandible or jaw bone varies from individual to individual. For example, some patients having disturbances of the tempromandibular joint are not capable of protruding and retruding their mandibles to the same extent as healthy individuals. Accordingly, before fitting patients with prosthetic or therapeutic dental appliances, it is important to accurately measure the range of movement of the patient's mandible in order to reduce the possibility of tempromandibular joint discomfort and post-insertion adjustment time. This is particularly true of dental appliances used in the treatment of sleep apnea and snoring which are designed to maintain the patient's mandible in a protruded position during sleep in order to prevent occlusion of the pharyngeal airway. However, the same concerns arise during the fabrication of other dental appliances, such as nightguards for preventing nocturnal bruxism (teeth grinding).

Scanning x-ray machines are often used by dental professionals for assessing a patient's mandibular range of movement. However, the cost of x-rays cannot be justified for routine assessments, and it is difficult to calibrate the x-ray results when casting dental molds.

"Gothic Arch" tracers are known in the prior art for providing a more direct, graphic representation of the natural range of movement of a patient's mandible. Gothic arch tracings can be produced by fitting the patient with upper and lower wax bite blocks and having the patient move his or her jaw between fully retruded and protruded positions and laterally excursive positions. This results in a wax tracing representative of the range of mandibular movement.

Existing gothic arch tracing techniques suffer from various shortcomings. In most cases, the tracing is produced internally of the patient's mouth and hence the quality and character of the tracing can not be monitored by supervising dental personnel. Another drawback is that prior art devices such as the Hanau instrument, which produce tracings etched into a wax substrate, are not readily reusable for other patients. Rather, a high degree of customization of the tracing apparatus for different patients is required which increases the cost and time required to complete the procedure.

Accordingly, the need has arisen for a reusable kit and technique for quickly and accurately generating external gothic arch tracings and for using such tracings in the fabrication of dental bite registration molds.

SUMMARY OF THE INVENTION

In accordance with the invention, a kit for fabricating a dental bite registration mold for a patient is disclosed. The kit includes a first bit rim adapted for engaging the patient's mandibular dentition. The first bite rim has a U-shaped arch for receiving a hardenable dental putty and a flat tracing plate connected to the arch for extending externally of the patient's mouth. A second bite rim adapted for engaging the patient's maxillary dentition is also provided. The second bite rim has a second U-shaped arch for receiving hardenable dental putty and an elongated tracing arm connected to the second arch for extending externally of the patient's mouth overlying the tracing plate. The kit also includes an adjustable stylus releasably connectible to the tracing arm for extending between the tracing arm and the tracing plate.

A removable paper substrate is attachable to the upper surface of the tracing plate. A first end of the stylus comprises a marker for drawing a tracing on the paper substrate when the patient moves the first bite rim relative to the second bit rim during mandibular motions.

Preferably, a second end of the stylus comprises a spring-loaded alignment pin insertable into an aperture formed in the tracing plate. The stylus may be threadedly connectible to the tracing arm.

The first and second arches include a plurality of spaced-apart retention apertures to facilitate bonding of the dental putty to the first and second bite rims. The kit may also include a separator plate insertable into the patient's mouth between the first and second bit rims while the dental putty is setting in order to prevent bonding of the first and second bit rims together.

A method of tracing the range of movement of a patient's mandible is also disclosed which comprises the steps of (a) fitting the patient with a first bite rim having a casting conforming to the patient's mandibular dentition and a flat tracing plate extending externally of the patient's mouth; (b) fitting the patient with a second bite rim having a casting conforming to the patient's maxillary dentition and having a tracing arm extending externally of the patient's mouth above the tracing plate; (c) securing a removable substrate to an upper surface of the tracing plate; (d) releasably securing a stylus to the tracing arm, the stylus having a first end for engaging the substrate; and (e) moving the patient's mandible between protruded and retruded positions and between laterally excursive positions so that the stylus draws a tracing on the substrate indicative of the range of movement of the patient's mandible.

A method of fabricating a dental bite registration mold for a patient is also disclosed which comprises the steps of (a) providing a first bite rim having a first U-shaped arch and a flat tracing plate extending forwardly of the first arch; (b) providing a second bite rim having a second U-shaped arch and a tracing arm extending forwardly of the second arch; (c) placing pliable dental putty into forward portions of the first and second arches; (d) inserting the first bite rim into the patient's mouth such that the dental putty in the first arch conforms to the patient's mandibular dentition and the tracing plate extends externally of the patient's mouth; (e) inserting a separator plate into the patient's mouth overlying the first bite rim; (f) inserting the second bite rim into the patient's mouth overlying the separator plate such that the dental putty in the second arch conforms to the patient's maxillary dentition and the tracing arm extends externally of the patient's mouth overlying the tracing plate; (g) allowing the dental putty to set with the patient biting firmly on the separator plate to obtain castings of at least the anterior segment of the patient's teeth; (h) removing the separator plate from the patient's mouth after the castings have set; (i) securing a removable substrate to the upper surface of the tracing plate; (j) releasably securing a stylus to the tracing arm and adjusting the stylus until the first end thereof engages the substrate; and (k) moving the patient's mandible between protruded and retruded positions and between laterally excursive positions so that the stylus draws a tracing on the substrate representative of the full range of movement of the patient's mandible.

The fabricating method may further include the steps of (1) removing the first and second bite rims from the patient's mouth; (m) marking the substrate at a predetermined point on the tracing; and (n) drilling a hole through the substrate and the tracing plate at the predetermined point.

The fabricating method may still further include the steps of (o) placing pliable dental putty on rearward portions of the first and second arches; (p) releasably securing an alignment pin to the tracing arm for extending between the tracing arm and the tracing plate; (q) reinserting the first and second bite rims into the patient's mouth so that the castings engage the patient's mandibular and maxillary incisors and the pliable putty conforms to at least the posterior segment of the patient teeth; (r) moving the patient's mandible until the spring-loaded pin is seated in the hole drilled in the tracing plate; (s) allowing the dental putty to set to obtain castings of the posterior teeth; and (t) removing the first and second bite rims and the alignment pin from the patient's mouth.

BRIEF DESCRIPTION OF THE DRAWINGS

In drawings which illustrate the preferred embodiment of the invention, but which should not be construed as limiting the spirit or scope of the invention in any way.

DETAILED DESCRIPTION OF THE PREFERRED EMBODIMENT

This application relates to a kit generally designated 10 for producing a gothic arch tracing representative of the range of movement of a patient's mandible. As discussed in further detail below, kit 10 is also used for fabricating a dental bite registration mold for the patient which can be used to mount casts of the patient's dentition in a specific relationship as required for prosthetic or therapeutic dental appliances, such as anti-snoring devices.

Figure 1:
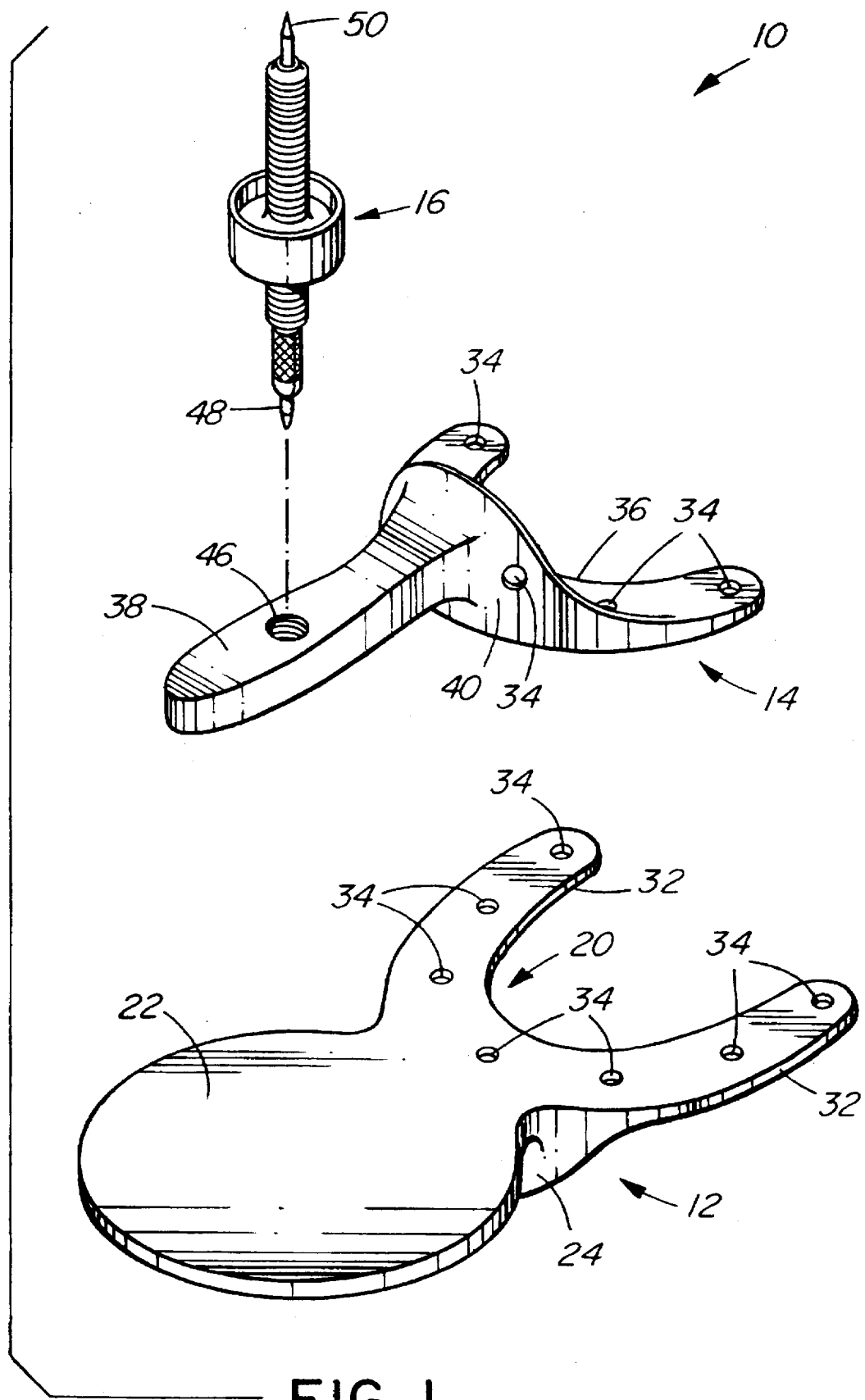
FIG. 1 is an exploded, isometric view illustrating the mandibular and maxillary bite rims and stylus comprising the applicant's gothic arch tracing kit.

With reference to FIG. 1, kit 10 includes a mandibular bite rim 12, a maxillary bite rim 14, and a stylus 16. Mandibular bite rim 12 includes a generally U-shaped mandibular arch 20 and a flat tracing plate 22 which is connected to arch 20 and extends forwardly therefrom. In the illustrated embodiment, tracing plate 22 is generally circular in shape although other shapes would also be suitable.

Figure 2:
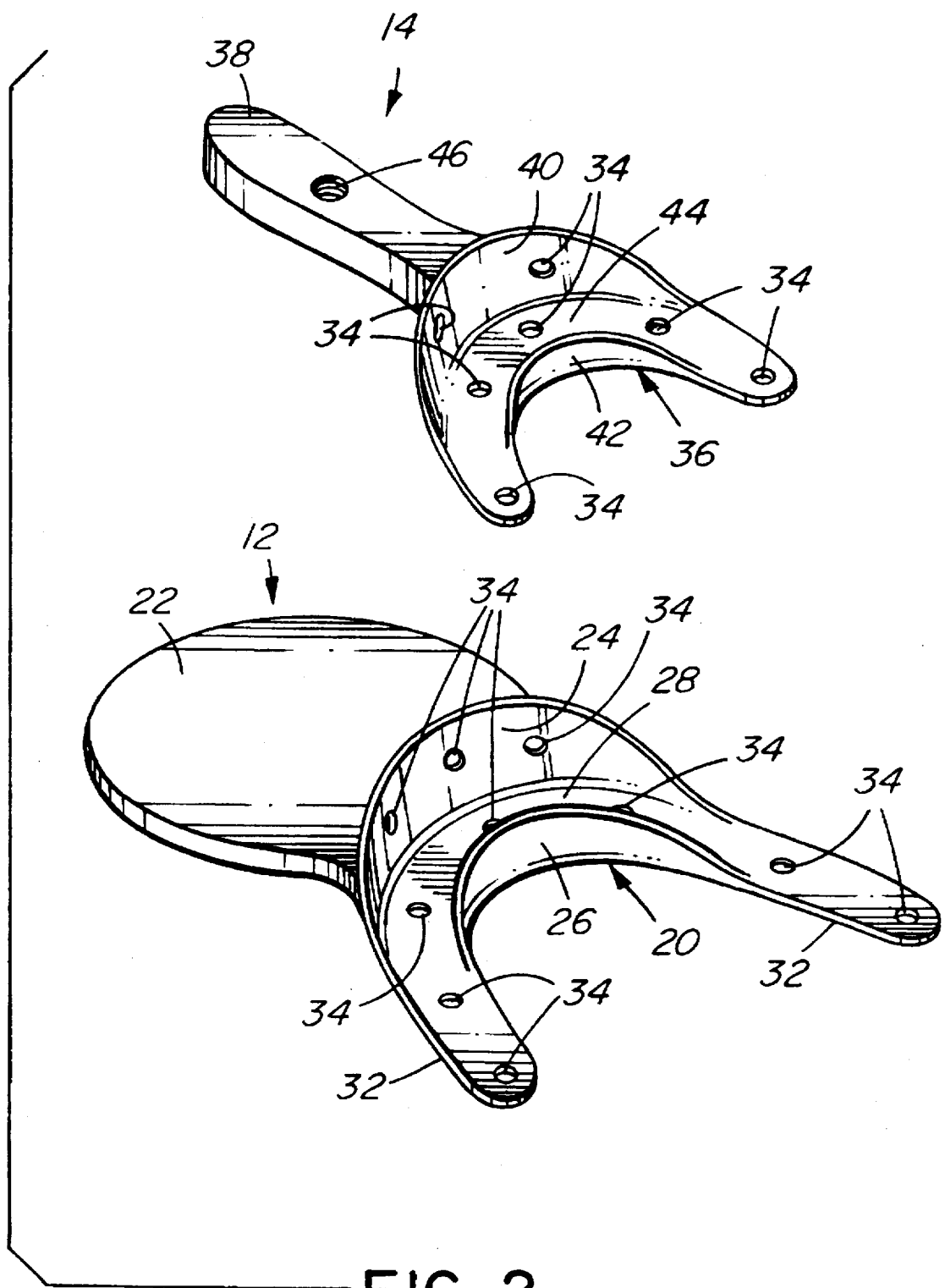
FIG. 2 is an isometric view of the mandibular and maxillary bite rims.
Figure 3:
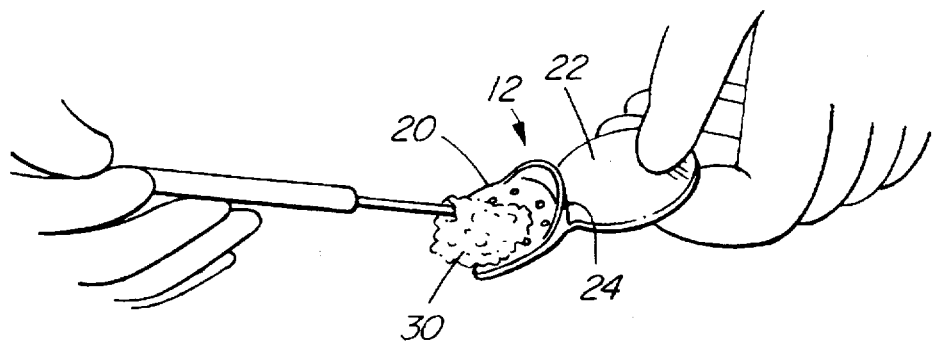
FIG. 3 is an schematic view illustrating the procedure for placing pliable dental putty onto the mandibular bite rim.

As shown best in FIG. 2, mandibular arch 20 includes an upstanding, curved forward wall 24 and a somewhat smaller curved rear wall 26 which together define a trough 28 for receiving pliable dental putty 30 used in the casting of dental impressions (FIG. 3). As should be apparent to someone skilled in the art, any thermoplastic or vinylpolysiloxine-based dental putty would be suitable for this purpose. Mandibular arch 20 also includes two opposed forks 32 which extend rearwardly of trough 28. Preferably a plurality of spaced-apart retention holes 34 are formed in mandibular arch 20 to facilitate bonding of dental putty 30 to mandibular bite rim 12 during the casting process described in further detail below.

Maxillary bite rim 14 includes a truncated U-shaped maxillary arch labelled 36 and a elongated tracing arm 38 extending forwardly therefrom. As shown in FIG. 2, maxillary arch 36 has an upstanding curved forward wall 40 and a somewhat smaller rear wall 42 which define a trough 44. Like mandibular trough 28, maxillary trough 44 is provided for receiving pliable dental putty. Maxillary arch 36 also includes a plurality of spaced-apart retention holes 34 to facilitate bonding of putty 30 to bite rim 14 during the casting process.

As shown best in FIG. 1, tracing arm 38 includes an internally threaded aperture 46 for releasably receiving stylus 16. Stylus 16 is an externally threaded screw having a marker 48, such as a spring-loaded lead pencil, mounted at one end thereof and a spring-loaded alignment pin 50 mounted at the other end thereof.

FIGS. 3–7 illustrate the series of steps which comprise the inventor's technique for producing a gothic arch tracing and for using such tracing to fabricate a dental bite registration mold. As shown in FIG. 3, the first step in the procedure is to fill an anterior portion of mandibular arch 20 with a supply of pliable dental putty 30. This is achieved by placing dental putty 30 into mandibular trough 28. A supply of dental putty 30 is similarly placed into maxillary trough 44.

Figure 4:
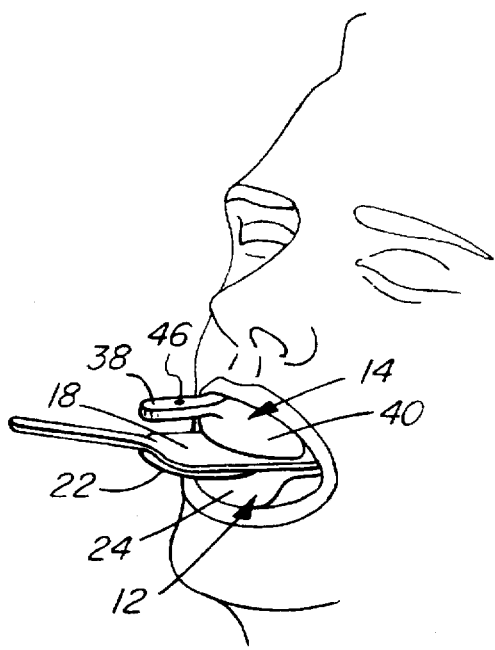
FIG. 4 is a schematic view showing the mandibular and maxillary bite rims fitted in the patient's mouth together with a separator plate.

Mandibular bite rim 12 is then seated in the patient's mouth so that the dental putty in trough 28 conforms to the anterior segment of the patient's mandibular dentition (i.e. the incisors and cuspids) and the large circular tracing plate 22 extends externally of the patient's mouth. As shown in FIG. 4, a separating plate 18 is then inserted into the patient's mouth directly overlying mandibular bite rim 12. Maxillary bite rim 14 is then seated so that the pliable putty in trough 44 engages the anterior segment of patient's maxillary dentition and tracing arm 38 extends externally of the patient's mouth centred above tracing plate 22.

The patient is then instructed to bite firmly on separator plate 18. The supervising dental personnel should ensure that tracing plate 22 and tracing arm 38 remain properly centred. Separator plate 18 may be precooled to decrease the setting time of dental putty 30 (this step is not required for polyvinyl putty). As the patient bites against separator plate 18, dental putty 30 is extruded through retention holes 34 and may be smoothed by the supervising dental personnel against the surface of arches 20, 36. Separator plate 18 is provided for preventing bonding of dental putty introduced into the respective mandibular and maxillary bite rims 12, 14.

Bite rims 12 and 14 should be left in the patient's mouth long enough to allow the dental putty to set. If necessary, bite rims 12, 14 may be removed and reseated into the patient's mouth while dental putty 30 is still pliable to ensure an easy ingress and egress over the patient's teeth. After putty 30 has set sufficiently to hold its own shape, bite rims 12, 14 may be removed from the patient's mouth and placed in cold water to expedite setting if necessary.

Figure 5A:
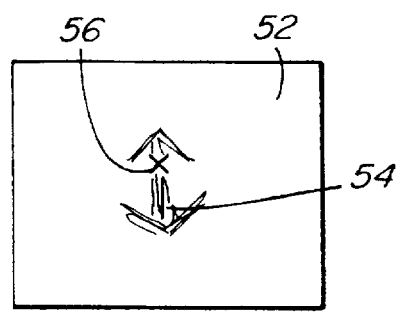
FIG. 5(a) is an enlarged view of a gothic arch tracing drawn on a paper substrate.
Figure 5:
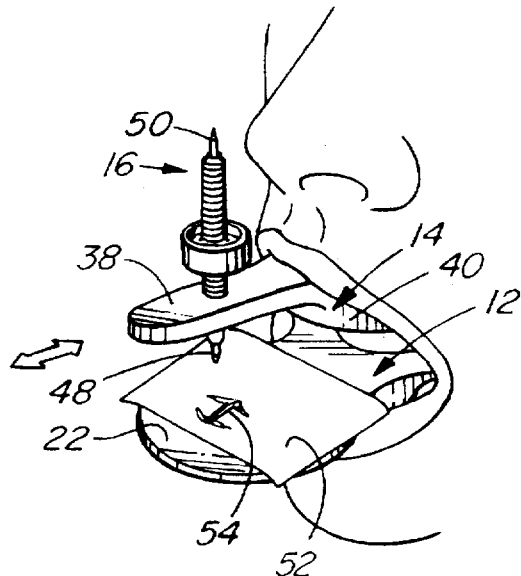
FIG. 5 is a schematic view showing the procedure for producing a gothic arch tracing.

The next step in the procedure as shown in FIG. 5 is to apply a removable sheet of paper substrate 52, such as a "post-it" note, to the upper surface of tracing plate 22. Stylus 16 is screwed into hole 46 in tracing arm 38 so that the stylus marker 48 touches the surface of paper substrate 52 when bite rims 12, 14 are fully reinserted into the patient's mouth. Stylus 16 may be readily adjusted to vary the degree of contact between stylus marker 48 and substrate 52 to ensure a smooth passage of stylus 16 over substrate 52.

The patient is then instructed to move his or her mandible between a fully retruded (i.e. centric) position and a fully protruded position, and between laterally excursive positions (starting from a retruded or protruded position). As shown in FIGS. 5 and 5(a), this results in a tracing 54 on paper substrate 52 resembling a "gothic arch" which is representative of the natural range of movement of the patient's mandible. If tracing 54 is not acceptable, then paper substrate 52 may be readily removed and replaced and the tracing procedure repeated.

Once an acceptable tracing 54 has been obtained, the range of movement of the patient's mandible should preferably be measured and recorded. As shown in FIG. 5(a), a mark 56 may then be placed on tracing 54 at a predetermined location. For example, if the patient's dental bite registration mold is to be used in the fabrication of a dental appliance for the treatment of sleep apnea and snoring as described in the inventor's co-pending P.C.T. application filed 10 Dec., 1993, then mark 56 is preferably placed along the mid-line of tracing 54 at approximately 60 percent of the patient's full protrusive range (i.e. slightly offset towards the forward end of the tracing). If the bite registration mold is to be used for other prosthetic or therapeutic purposes, such as a nightguard for treatment of teeth grinding, then mark 56 may be placed by the dental personnel at some other suitable predetermined location.

Figure 6:
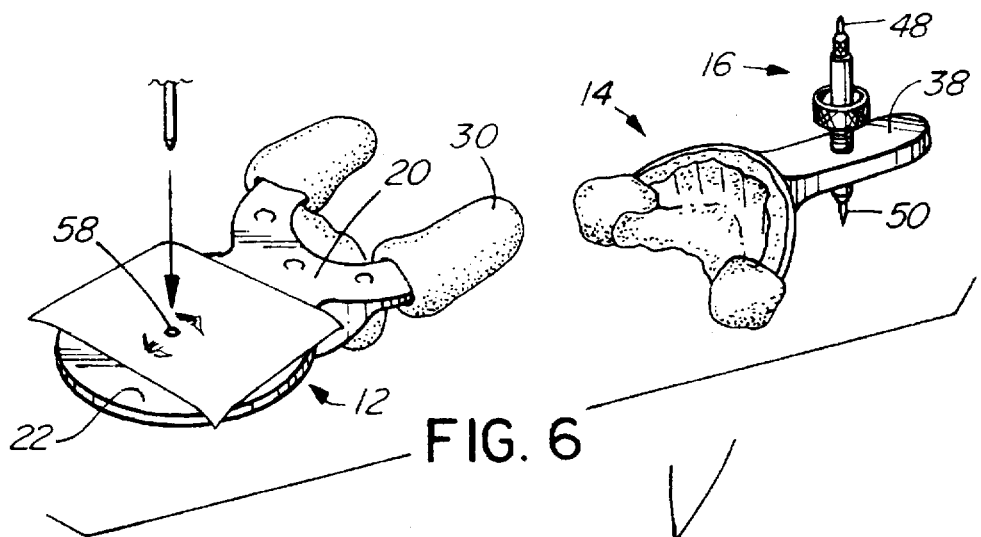
FIG. 6 illustrates the procedure for drilling a hole in the paper substrate and tracing plate at a predetermined location and for applying a second supply of putty to the bite rims.

As shown in FIG. 6, the next step in the procedure is to drill a small hole 58 through paper substrate 52 and tracing plate 22 at the location of mark 56 after bite rims 12, 14 have been removed from the patient's mouth. After hole 58 has been drilled, the paper substrate 52 may be removed from tracing plate 22 and placed in the patient's file so that a record of tracing 54 is retained for future reference.

The next stage in the procedure is to unscrew stylus 16 from tracing arm 38 and then re-screw stylus 16 into position in the opposite direction so that spring-loaded alignment pin 50 extends downwardly to engage tracing plate 22 (FIG. 6). As should be apparent to someone skilled in the art, stylus marker 48 and alignment pin 50 could be completely separate elements rather than being formed at either end of stylus 16.

Figure 7:
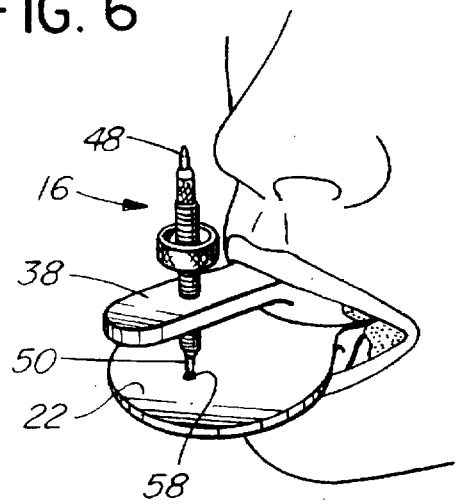
FIG. 7 illustrates the procedure for aligning the bite rims at the preferred location.

Another supply of pliable dental putty 30 is then placed on the rearward portions of bite rim troughs 28 and 44 and on rearwardly extending forks 32 as shown in FIG. 6. Bite rims 12 and 14 are then re-seated into the patient's mouth and the patient is asked to bite so that dental putty 30 conforms to the mandibular and maxillary molar teeth. The patient is then instructed to move his or her mandible until spring-loaded alignment pin 50 drops into hole 58 drilled in tracing plate 22 (FIG. 7). The patient is asked to swallow in order to force the tongue against the setting dental putty inside the patient's mouth and ensure a good adaptation to the lingual surfaces of the teeth. As described above, the setting dental putty is extruded through retention holes 34 formed in arches 20, 36 in order to ensure good adhesion between the dental putty and bite rims 12, 14. The supervising dental personnel may use their fingers to smooth any excess putty against the buccal surfaces of the teeth.

Figure 8:
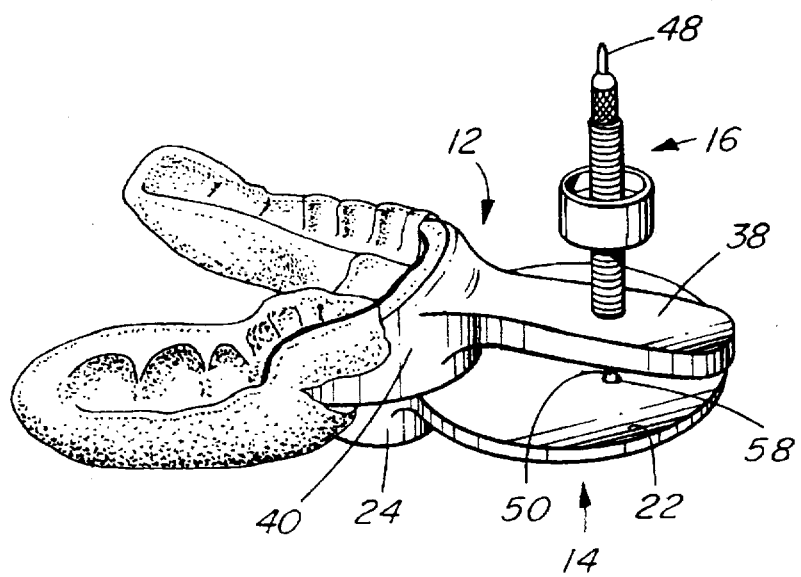
FIG. 8 is an isometric view of the completed bite registration mold.

Bite rims 12, 14 are left in the patient's mouth until the second supply of dental putty is fully set and a unitary dental bite registration mold has been formed. Bite rims 12, 14 and stylus 16 comprising the bite registration mold are then removed from the patient's mouth to complete the procedure (FIG. 8).

The patient's bite registration mold may then be used to fabricate the desired dental appliance, such as an anti-snoring device designed in maintain the patient's mandible in a protruded position. As discussed above, bite registration mold may also be used to cast other prosthetic or therapeutic dental appliances as required. The mold ensures that the upper and lower castings of the patient's dentition will be positioned in a precise, predetermined relationship.

After the desired dental appliance has been fabricated, dental putty 30 may be stripped off bite rims 12 and 14 and hole 58 drilled in tracing plate 22 may be quickly filled with a fast-setting acrylic. All of the components of tracing kit 10, including mandibular bite rim 12, maxillary bit rim 14, stylus 16 and separator plate 18 may then be reused on another patient.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method of fabricating a dental bite registration mold comprising the steps (a) providing a first bite rim having a first U-shaped arch and a flat tracing plate extending forwardly of said first arch;

(a) providing a second bite rim having a second U-shaped arch and a tracing arm extending forwardly of said second arch;

(c) placing pliable dental putty into forward portions of said first and second arches;

(d) inserting said first bite rim into said patient's mouth such that said dental putty in said first arch conforms to an anterior segment of said patient's mandibular dentition and said tracing plate extends externally of said patient's mouth;

(e) inserting a separator plate into said patient's mouth overlying said first bite rim;

(f) inserting said second bite rim into said patient's mouth overlying said separator plate such that said dental putty in said second arch conforms to an anterior segment of said patient's maxillary dentition and said tracing arm extends externally of said patient's mouth overlying said tracing plate;

(g) allowing said dental putty to set with said patient biting firmly on said separator plate to obtain castings of said anterior segments of said patient's mandibular dentition and maxillary dentition;

(h) removing said separator plate from said patient's mouth;

(i) securing a removable substrate to an upper surface of said tracing plate;

(j) releasably securing a stylus to said tracing arm and adjusting said stylus until a first end thereof engages said substrate;

(k) moving said patient's mandible between protruded and retruded positions and between laterally excursive positions so that said stylus draws a tracing on said substrate indicative of the range of movement of said patient's mandible;

(l) removing said first and second bite rims from said patient's mouth;

(m) marking said substrate at a pre-determined point on said tracing;

(n) drilling a hole through said substrate and said tracing plate at said pre-determined point;

(o) placing pliable dental putty around rearward portions of said first and second arches;

(p) releasably securing an alignment pin to said tracing arm for extending between said tracing arm and said tracing plate;

(q) reinserting said first and second bite rims into said patient's mouth so that said castings engage said anterior segments of said patient's teeth and said pliable putty conforms to posterior segments of said patient's teeth;

(r) moving said patient's mandible until said spring-loaded pin is seated in said hole drilled in said tracing plate;

(s) allowing said dental putty to set to obtain castings of said posterior teeth segments; and (t) removing said first and second bite rims and said pin from said patient's mouth.

2. The fabricating method of claim 1, wherein the end of said alignment pin engaging said tracing plate is spring-loaded.

3. The fabricating method of claim 2, wherein said first end of said stylus comprises a lead marker.

4. The fabricating method of claim 3, wherein said marker and said alignment pin are formed on opposite ends of said stylus.

5. The fabricating method of claim 3, wherein said removable substrate is a sheet of paper.

6. A method of fabricating a dental bite registration mold comprising the steps of:

(a) providing a first bite rim having a first U-shaped arch and a flat tracing plate extending forwardly of said first arch;

(a) providing a second bite rim having a second U-shaped arch and a tracing arm extending forwardly of said second arch;

(c) placing pliable dental putty into forward portions of said first and second arches;

(d) inserting said first bite rim into said patient's mouth such that said dental putty in said first arch conforms to said patient's mandibular dentition and said tracing plate extends externally of said patient's mouth;

(e) inserting a separator plate into said patient's mouth overlying said first bite rim;

(f) inserting said second bite rim into said patient's mouth overlying said separator plate such that said dental putty in said second arch conforms to said patient's maxillary dentition and said tracing arm extends externally of said patient's mouth overlying said tracing plate;

(g) allowing said dental putty to set with said patient biting firmly on said separator plate to obtain castings of at least an anterior segments of said patient's teeth;

(h) removing said separator plate from said patient's mouth;

(i) securing a removable substrate to an upper surface of said tracing plate;

(j) releasably securing a stylus to said tracing arm and adjusting said stylus until a first end thereof engages said substrate;

(k) moving said patient's mandible between protruded and retruded positions and between laterally excursive positions so that said stylus draws a tracing on said substrate indicative of the range of movement of said patient's mandible;

(l) removing said first and second bite rims from said patient's mouth;

(m) marking said substrate at a pre-determined point on said tracing;

(n) drilling a hole through said substrate and said tracing plate at said pre-determined point;

(o) placing pliable dental putty on rearward portions of said first and second arches;

(p) releasably securing an alignment pin to said tracing arm for extending between said tracing arm and said tracing plate;

(q) reinserting said first and second bite rims into said patient's mouth so that said castings engage said anterior segments of said patient's teeth and said pliable putty conforms to posterior segments of said patient's teeth;

(r) moving said patient's mandible until said spring-loaded pin is seated in said hole drilled in said tracing plate;

(s) allowing said dental putty to set to obtain castings of said posterior teeth segments; and (t) removing said first and second bite rims and said pin from said patient's mouth, wherein said first end of said stylus comprises a spring-loaded lead marker and wherein said alignment pin is formed on a second end of said stylus opposite said first end.

* * * * *